United States Patent
Tonelli et al.

(10) Patent No.: US 7,517,332 B2
(45) Date of Patent: Apr. 14, 2009

(54) INFUSION DEVICE FOR MEDICAL FLUIDS

(75) Inventors: Claudio Tonelli, Modena (IT); Andrea Ligabue, San Prospero (IT); Silvano Cestari, San Felice sul Panaro (IT)

(73) Assignee: Gambro Lundia AB, Lund (SE)

( * ) Notice: Subject to any disclaimer, the term of this patent is extended or adjusted under 35 U.S.C. 154(b) by 245 days.

(21) Appl. No.: 11/104,447

(22) Filed: Apr. 13, 2005

(65) Prior Publication Data

US 2005/0234382 A1 Oct. 20, 2005

Related U.S. Application Data

(60) Provisional application No. 60/522,442, filed on Oct. 1, 2004.

(30) Foreign Application Priority Data

Apr. 20, 2004 (IT) .......................... MO2004A0085

(51) Int. Cl.
| | |
|---|---|
| A61M 37/00 | (2006.01) |
| A61M 1/00 | (2006.01) |
| B67D 5/30 | (2006.01) |
| F04B 49/00 | (2006.01) |
| A61M 31/00 | (2006.01) |
| B67D 5/22 | (2006.01) |
| B65D 88/54 | (2006.01) |
| G01F 11/00 | (2006.01) |
| F04B 49/06 | (2006.01) |
| F04B 17/00 | (2006.01) |

(52) U.S. Cl. .......................... 604/4.01; 604/31; 604/48; 604/65; 604/93.01; 222/22; 222/31; 222/41; 222/46; 222/63; 222/325; 222/333; 222/390; 417/15; 417/20; 417/44.4; 417/44.2; 417/63; 417/410.1; 417/476

(58) Field of Classification Search .................... 604/65, 604/67, 93.01, 131, 154, 155; 128/DIG. 12, 128/DIG. 13; 417/20, 53, 63, 474; 705/3.2; 222/23, 55, 63, 333
See application file for complete search history.

(56) References Cited

U.S. PATENT DOCUMENTS 4,137,913 A * 2/1979 Georgi .......................... 604/67

(Continued)

FOREIGN PATENT DOCUMENTS

DE  4 000 873  7/1991

(Continued)

OTHER PUBLICATIONS

Online encyclopedia article, "Stiffness" accessed Apr. 9, 2008. http://en.wikipedia.org/wiki/Stiffness.*

*Primary Examiner*—Leslie Deak
*Assistant Examiner*—Adam Marcetich
(74) *Attorney, Agent, or Firm*—Rissman Jobse Hendricks & Oliverio LLP

(57) ABSTRACT

An infusion device comprises a pusher for a plunger of a syringe containing a liquid to be infused. A load cell measures the push force. An encoder associated to a motor commanding the pusher measures the displacement of the pusher. A controller signals an alarm when the ratio between the variation of the push force and the displacement exceeds a predetermined threshold. The device, which serves for infusing an anticoagulant into an extracorporeal blood circuit in a dialysis apparatus, is able to signal an onset of an anomalous situation of lack of infusion in good time.

9 Claims, 6 Drawing Sheets

U.S. PATENT DOCUMENTS

| | | | | |
|---|---|---|---|---|
| 4,269,185 | A | * 5/1981 | Whitney et al. | 604/135 |
| 4,435,173 | A | * 3/1984 | Siposs et al. | 604/155 |
| 4,500,309 | A | * 2/1985 | Diederich et al. | 604/6.06 |
| 4,529,401 | A | * 7/1985 | Leslie et al. | 604/131 |
| 4,533,346 | A | * 8/1985 | Cosgrove et al. | 604/66 |
| 4,652,260 | A | * 3/1987 | Fenton et al. | 604/67 |
| 4,696,671 | A | * 9/1987 | Epstein et al. | 604/67 |
| 4,731,058 | A | 3/1988 | Doan | |
| 5,059,171 | A | * 10/1991 | Bridge et al. | 604/67 |
| 5,242,408 | A | 9/1993 | Jhuboo et al. | |
| 5,244,461 | A | * 9/1993 | Derlien | 604/65 |
| 5,295,967 | A | 3/1994 | Rondelet et al. | |
| 5,501,665 | A | 3/1996 | Jhuboo et al. | |
| 5,520,637 | A | * 5/1996 | Pager et al. | 604/66 |
| 5,647,853 | A | 7/1997 | Feldmann et al. | |
| 6,200,289 | B1 | * 3/2001 | Hochman et al. | 604/67 |
| 6,269,340 | B1 | 7/2001 | Ford et al. | |
| 6,423,029 | B1 | 7/2002 | Elsberry | |
| 6,423,035 | B1 | 7/2002 | Das et al. | |
| 7,118,347 | B2 | * 10/2006 | Solgaard et al. | 417/12 |
| 2001/0034502 | A1 | 10/2001 | Moberg et al. | |
| 2002/0128594 | A1 | 9/2002 | Das et al. | |
| 2003/0073954 | A1 | 4/2003 | Moberg et al. | |
| 2004/0015124 | A1 | 1/2004 | Sciulli et al. | |
| 2004/0133166 | A1 | 7/2004 | Moberg et al. | |

FOREIGN PATENT DOCUMENTS

| | | |
|---|---|---|
| DE | 4 220 831 | 4/1994 |
| EP | 0 278 146 | 8/1988 |
| EP | 0 319 648 | 6/1989 |
| EP | 0 402 553 | 12/1990 |
| EP | 0 319 648 | 1/1992 |
| EP | 0 589 328 | 3/1994 |
| EP | 0 916 353 | 5/1999 |
| EP | 1 066 846 | 1/2001 |
| EP | 1 188 454 | 3/2002 |
| EP | 1 350 527 A2 | 10/2003 |
| EP | 1 362 606 | 11/2003 |
| FR | 2 757 772 | 7/1999 |
| GB | 2 224 444 | 5/1990 |
| GB | 2 356 349 | 5/2001 |

\* cited by examiner

INFUSION DEVICE FOR MEDICAL FLUIDS

CROSS-REFERENCE TO RELATED APPLICATIONS

This application claims the benefit of priority of U.S. provisional application no. 60/522,442, filed Oct. 1, 2004, and Italian patent application no. MO2004A000085, filed Apr. 20, 2004, both of which are incorporated herein by reference in their entirety.

BACKGROUND OF THE INVENTION

The invention relates to an infusion device for medical fluids, in particular for an extracorporeal blood circuit.

Specifically, though not exclusively, the invention can be usefully applied for infusing an anticoagulant in an extracorporeal circuit operatively associated with a machine for extracorporeal blood treatment.

Extracorporeal treatments usually include a removal of blood from the patient, external treatment thereof away from the human body, followed by its return, after treatment, into circulation.

Extracorporeal blood is made to circulate through a circuit comprising, in general, an arterial line, or blood removal line, which takes the blood from the patient to a blood treatment device (for example a dialyzer filter) and a venous line, or blood return line, which returns the treated blood to the patient.

To reduce the risk of coagulation of the extracorporeal blood, a known method includes infusion of an anticoagulant (for example heparin) into the extracorporeal circuit, generally into the arterial line, through an infusion line, with relatively low infusion flow rates.

An infusion device which is typically used in this method is a syringe pump, wherein a pushing element, on command of a linear actuator, pushes the plunger of a syringe containing the anticoagulant at an advancement rate which is predetermined and relatively slow. For example, in a dialysis treatment, usually the syringe contains the quantity of anticoagulant necessary for several hours of treatment. The pushing element and the actuator are part of the extracorporeal treatment machine (for example the dialysis machine), while the syringe is generally of the single-use type, or in any case is of the disposable type.

The prior art also teaches an infusion device for a security system against occurrence of overpressures internally of the syringe, due for example to occlusions in the infusion line, with a consequent interruption in the infusion flow.

The delay between the occurrence of an occlusion and its signalling, for example by an acoustic alarm or other form of alarm, is relevant in terms of patient safety. Clinical practice teaches that a loss of anticoagulant infusion for more than fifteen minutes can cause the formation of blood clots in the extracorporeal circuit which, if not quickly identified, can become nuclei of bigger and progressively-growing clots.

A safety system is described, for example, in EP 0 319 648, in which a syringe pump has a sensor for measuring the force acting on the syringe plunger, or on the frontal part of the syringe, and a calculator determines the pressure in the syringe, based on the force measured and the plunger area, previously entered in the calculator, and issues an alarm signal if a predefined maximum pressure threshold is exceeded.

In a further example, U.S. Pat. No. 5,295,967 describes a syringe pump comprising a force transducer for continuously monitoring the force on the syringe plunger, a microprocessor for converting the measured force into a syringe pressure reading, and a display on which the syringe pressure continuously appears in order for the syringe pressure to be monitored during pumping, and for any risk of occlusion to be quickly spotted.

U.S. Pat. No. 5,242,408 describes a security system against the risk of occlusion in a syringe pump, wherein the syringe pressure is calculated by means of a special algorithm, independently of any data regarding the transversal section of the syringe.

The prior art monitoring systems all however exhibit a drawback: they are not able, in good time, to signal a risk of occlusion in the infusion line when the infusion flow rate is very low, as happens for example in an infusion device of an anticoagulant in an extracorporeal circuit.

The above-cited security systems are based, essentially, on the fact that an occlusion along the infusion line leads to an increase in the pressure internally of the syringe. These known systems perform a monitoring of the pressure, emitting an alarm signal when a limit value is exceeded. However, in the case of low infusion flow rates of anticoagulant and/or use of syringes of large dimensions, an occlusion leads to a relatively slow change in the internal pressure of the syringe, and thus to a considerable delay in the alarm signal.

A further cause of delay in alarm signalling is the presence of a low pressure internally of the extracorporeal system, which tends to increase times for reaching the threshold conditions which determine an alarm signalling.

SUMMARY OF THE INVENTION

An aim of the present invention is to provide an infusion device provided with a security system able to signal an anomalous situation, relating to an occlusion in the blood flow, in good time.

A further aim of the invention is to make available a machine for extracorporeal blood treatment, provided with an infusion device having a security system that guarantees against undesired absence of infusion, even in cases of very low infusion flow rates, by signalling (in good time) any danger of occlusion in the infusion flow.

An advantage of the invention is that it provides an infusion device, constructionally simple and economical, provided with a system for signalling an insufficient infusion flow which is highly reliable and very precise.

A further advantage of the invention is that it provides a security system which signals, in good time, an anomalous situation which can be linked to an insufficient infusion flow and/or an overpressure.

These aims and advantages and more besides are all attained by the object of the invention, as it is characterised in one or more of the appended claims.

In an embodiment of the invention, the security system signals an anomalous situation if the derivative of a first parameter indicating the infusion force, compared to a second parameter indicating the progression of the infusion, is greater than a maximum threshold.

In an embodiment of the invention, the infusion force is a linear pushing force, usable for example in an infusion device comprising a pump of a syringe type.

In an embodiment of the invention, the above-cited second parameter is correlated to the displacement of a mobile part of the device.

In a specific embodiment of the invention, the derivative is calculated on the basis of at least one relation between a change in the first parameter and a corresponding change in the second parameter.

In an embodiment of the invention, the security system performs at least a second control to verify whether the infusion force exceeds a maximum threshold, predetermined or calculated using the read values of the first parameter.

In an embodiment of the invention, the security system performs at least a third control to verify if the infusion force falls below a minimum threshold, predetermined or calculated using the values actually detected for the first parameter.

Further characteristics and advantages of the present invention will better emerge from the detailed description that follows of at least an embodiment of the invention, illustrated by way of non-limiting example in the accompanying figures of the drawings.

BRIEF DESCRIPTION OF THE DRAWINGS

The description will now follow, with reference to the figures of the drawings, provided by way of non-limiting example, and in which.

DETAILED DESCRIPTION

Figure 1:
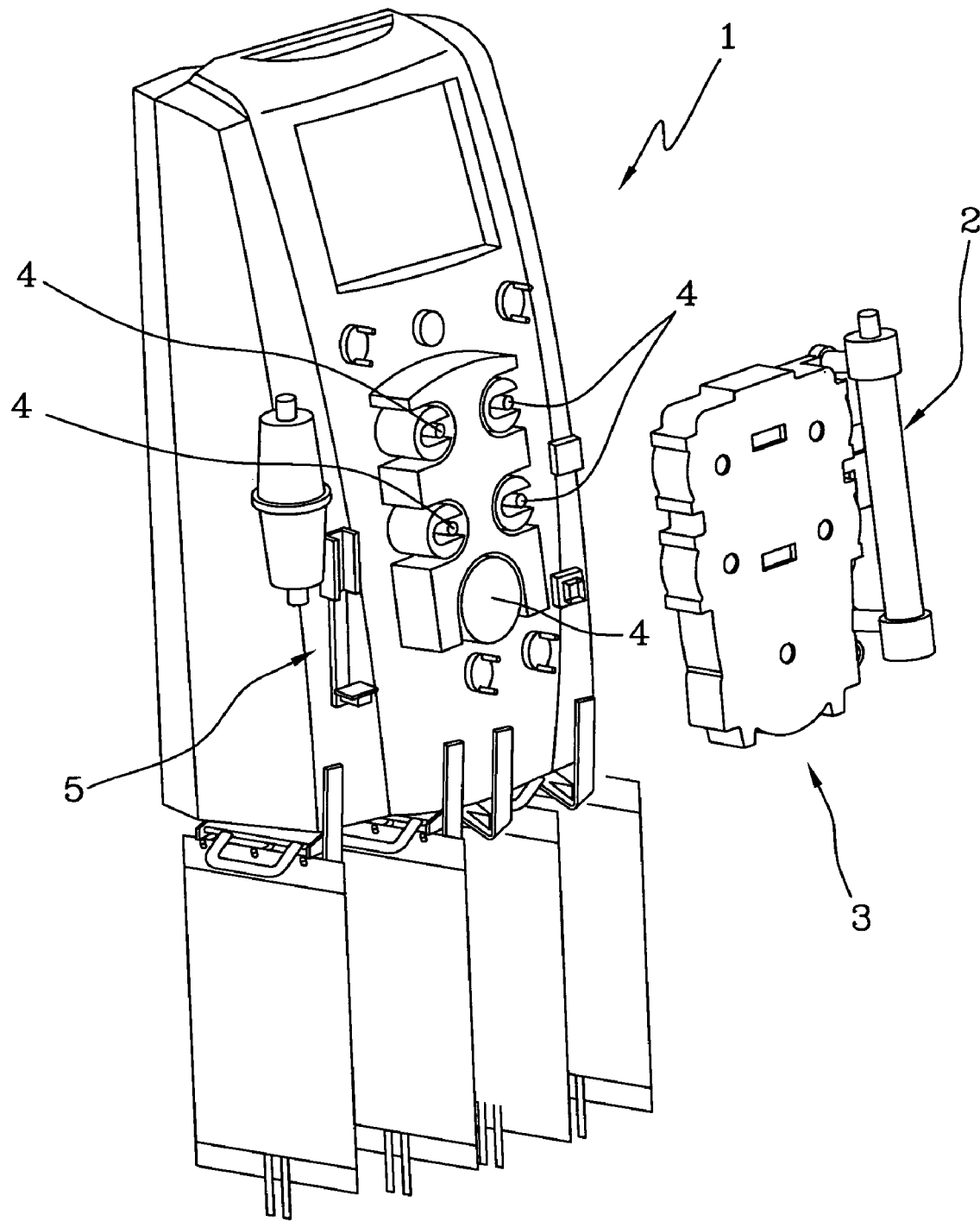
FIG. 1 shows a machine for extracorporeal blood treatment, provided with the infusion device of the invention.
Figure 2:
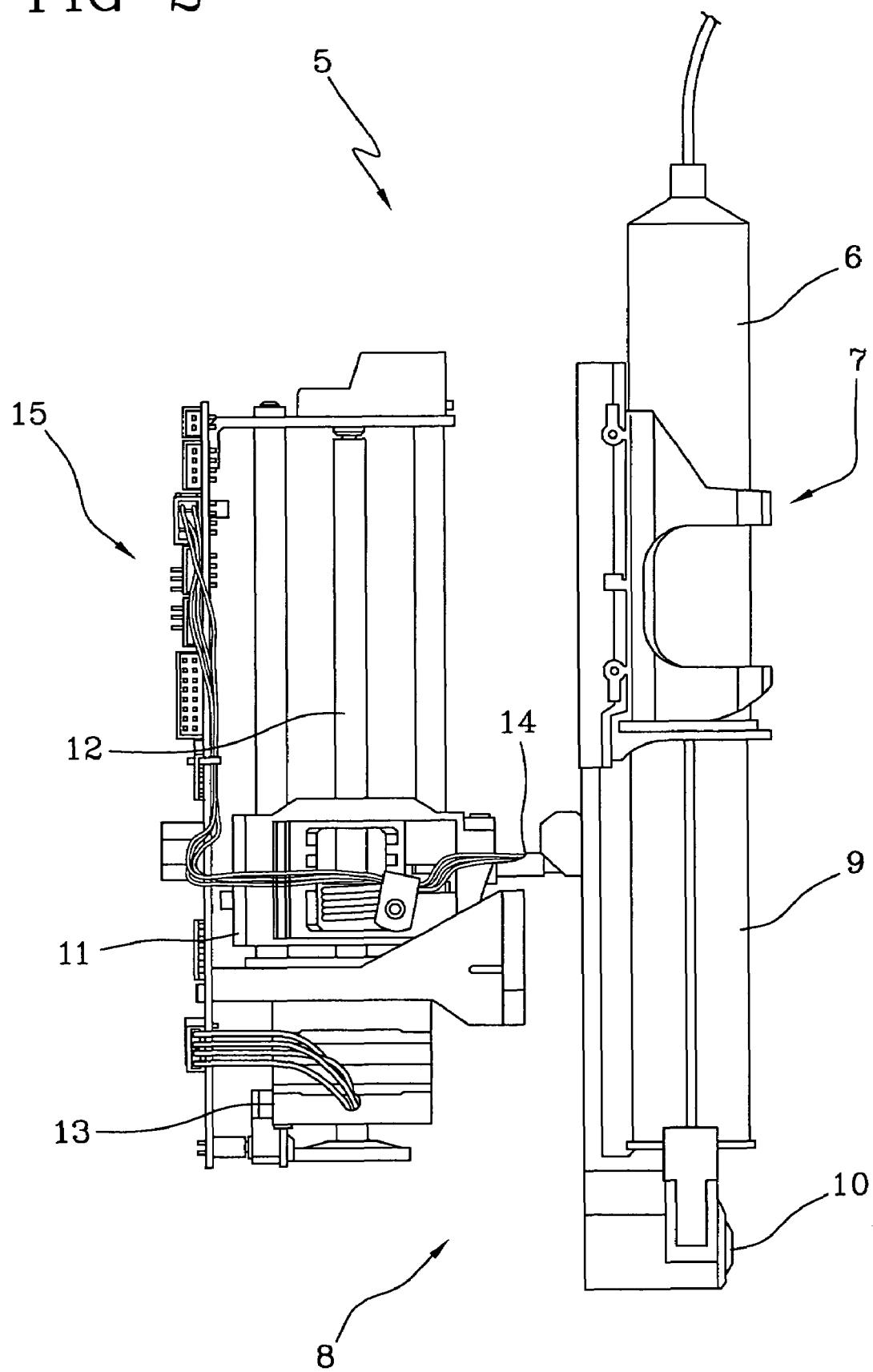
FIG. 2 shows, in greater detail and in enlarged scale, the infusion device of FIG. 1.

Legend of FIGS. 1 and 2.

1 Machine for extracorporeal blood treatment
2 Blood treatment device
3 Fluid distribution circuit
4 Tube deformation-type pumps (peristaltic)
5 Infusion device
6 Syringe
7 Syringe holder
8 Actuator of the infusion device
9 Syringe plunger
10 Actuator pusher
11 Actuator truck
12 Endless screw translator of actuator
13 Actuator motor
14 Force sensor
15 Actuator controller 1 denotes in its entirety a machine for extracorporeal blood treatment which, in the specific case, is a dialysis machine for treatment of renal insufficiency which can perform, selectively, the following treatments: hemodialysis, pure ultrafiltration, hemofiltration, hemodiafiltration, therapeutic plasma exchange. The machine of FIG. 1 is especially suitable for intensive treatment of acute kidney failure.

A blood treatment device 2 (dialyzer filter) is associated operatively with the dialysis machine 1; also associated thereto is a fluid distribution circuit 3 which is connected to the blood treatment device 2. In FIG. 1, for the sake of simplicity and clarity of the drawing, only the support for the fluid distribution circuit is associated to is shown. This circuit comprises, in particular, an extracorporeal blood circuit, provided with an arterial line and a venous line, as well as a circuit for circulation of various treatment fluids that can comprise, according to the selected treatment, a line supplying a fresh dialysis fluid to the treatment device 2, a discharge line for a used fluid exiting from the treatment device 2, one or more infusion lines of various medical liquids (substitution liquids, anticoagulant, etc). In the specific embodiment, the blood treatment device 2 and the fluid distribution circuit 3 are both of the single-use type, or are in any case of the dispensable type.

The machine 1 is further provided with means for circulating the various fluids along the lines, which means include various tube-deformation (peristaltic) pumps 4.

The means for circulating the anticoagulant comprise an infusion device 5, particularly suitable for administering liquids at low flow-rates. The infusion device 5, which is illustrated in greater detail in FIG. 2, comprises, in the illustrated embodiment, a syringe-type pump.

The infusion device 5, which is predisposed on a front panel of the machine 1, exhibits a housing for receiving a syringe 6 containing the anticoagulant to be infused. The machine 1 is further provided with means, of known type, for fixing the syringe in the housing, denoted by 7. The syringe 6 is connected to a line for infusion of anticoagulant which terminates in the arterial line.

The infusion device 5 comprises an actuator 8 destined to control the movement of the plunger 9 of the syringe. The actuator 8, which is a linear actuator, comprises a mobile part, mobile along a straight movement direction. The mobile part comprises a pusher 10 destined to interact contactingly with the plunger 9, in order to exert a pushing pressure for causing an infusion. The actuator 8 also comprises, in the present embodiment, a truck 11 which bears the pusher 10 and is guided by an endless screw translator 12 rotated by an electric motor 13, for example a step motor.

The infusion device 5 comprises a force sensor 14 for measuring a push force applied on the pusher 10. The force sensor 14 comprises, in the embodiment, an analog transducer of force (for example a load cell) which continuously measures the push force applied on the pusher 10.

In the illustrated embodiment, the force sensor 14 is arranged between the linearly mobile truck 11 and the pusher 10. Other arrangements can be made, however, for example in a housing zone of the syringe for operating on the front part of the syringe, or in other positions besides. The force sensor 14 enables a measurement to be taken of the infusion force applied on the plunger 9 of the syringe 6.

The infusion device 5 further comprises a second sensor for measuring the displacement of at least a mobile part of the linear actuator, i.e. the pusher 10 and/or the truck 11. The displacement sensor is, in the example, a magnetic encoder provided on the motor 13, which provides signals indicating the rotation angle of the endless screw translator 12. The signals enable a calculation of the linear displacement of the mobile part of the actuator 8.

The infusion device 5 comprises an automatic recognition system of a syringe 6 arranged in the housing. The recognition system can be, for example, an optical reader (of known type and not illustrated) able to recognise an identification sign located on the syringe 6 (for example, a bar code).

The infusion device 5 is also provided with a controller 15 which commands the actuator 8, and which receives the signals provided by the force sensor 14 and the displacement sensor (encoder located in the motor 13).

The reading of the force sensor is synchronised with the advancement of the linear actuator, so that the reading is updated at each step of the motor.

The controller 15 is programmed to carry out the following operations:

a) calculating at least one variation in the infusion force applied on the pusher 10 and at least one corresponding displacement of the pusher itself;
b) verifying whether the variation in the infusion force and the displacement are in a predetermined relation with a reference value;
c) emitting a signal in consequence of the above-mentioned verification.

Operation a), calculating the variations of the applied force and the corresponding displacements on force variation, includes the sub-phases of:

a1) acquiring a force value $F_1$ at instant $T_1$ from the displacement sensor; the value supplied by the displacement sensor is correlated to an angular position of the translator 12, which angular position is correlated, in a known way, with a linear position $x_1$ of the pusher 10;
a2) acquiring a force value $F_2$ at an instant $T_2$ from the force sensor 14 and a position value $x_2$ at instant $T_2$ from the displacement sensor, with $T_2=T_1+\Delta T$, where $\Delta T$ is a predetermined time interval;
a3) calculating the force variation $\Delta F=F_2-F_1$ and the displacement $\Delta x=x_2-x_1$; the linear displacement $\Delta x$ of the pusher 10 is calculable, in a known way, from the rotation of the translator 12 supplied by the encoder.

The verification operation b) comprises the sub-phases of:
b1) calculating the ratio between the variation in the force and the displacement $\Delta F/\Delta x$;
b2) comparing the ratio $\Delta F/\Delta x$ with a predetermined maximum threshold value $(\Delta F/\Delta x)_{max}$.

If $\Delta F/\Delta x<(\Delta F/\Delta x)_{max}$, the controller 15 continues to monitor the infusion device 5 without signalling an anomalous situation.

If $\Delta F/\Delta x \geq (\Delta F/\Delta x)_{max}$, the controller 15 emits an alarm signal to advise of the risk of occlusions forming in the infusion flow.

The above operation c) comprises emission of a signal for varying a predetermined state indicator, so as to signal the result of the verification of stage b).

The controller 15 performs another type of control in combination with the one described above. The controller 15 is also programmed to carry out the following operations, in combination with the ones already described:

d) verifying whether the force F applied on the pusher 10 is in a predetermined relation with at least one reference value;
e) emitting a signal in consequence of the second verification.

In particular, the controller 15 compares force $F_i$ on the pusher at time $T_i$ with a maximum threshold $F_{max}$ and with a minimum threshold $F_{min}$. If $F_i<F_{max}$, or if $F_i>F_{min}$, the controller 15 does not signal any anomaly, while if $F_i>F_{max}$, or if $F_i \leq F_{min}$, the controller 15 signals an alarm.

Exceeding the minimum threshold $F_{min}$ enables a detection of a possibly dangerous pressure condition inside the syringe, such as for example a risk of loss of anticoagulant from the syringe seal, or a loss of anticoagulant at some point between the syringe and the extracorporeal circuit.

Figure 4:
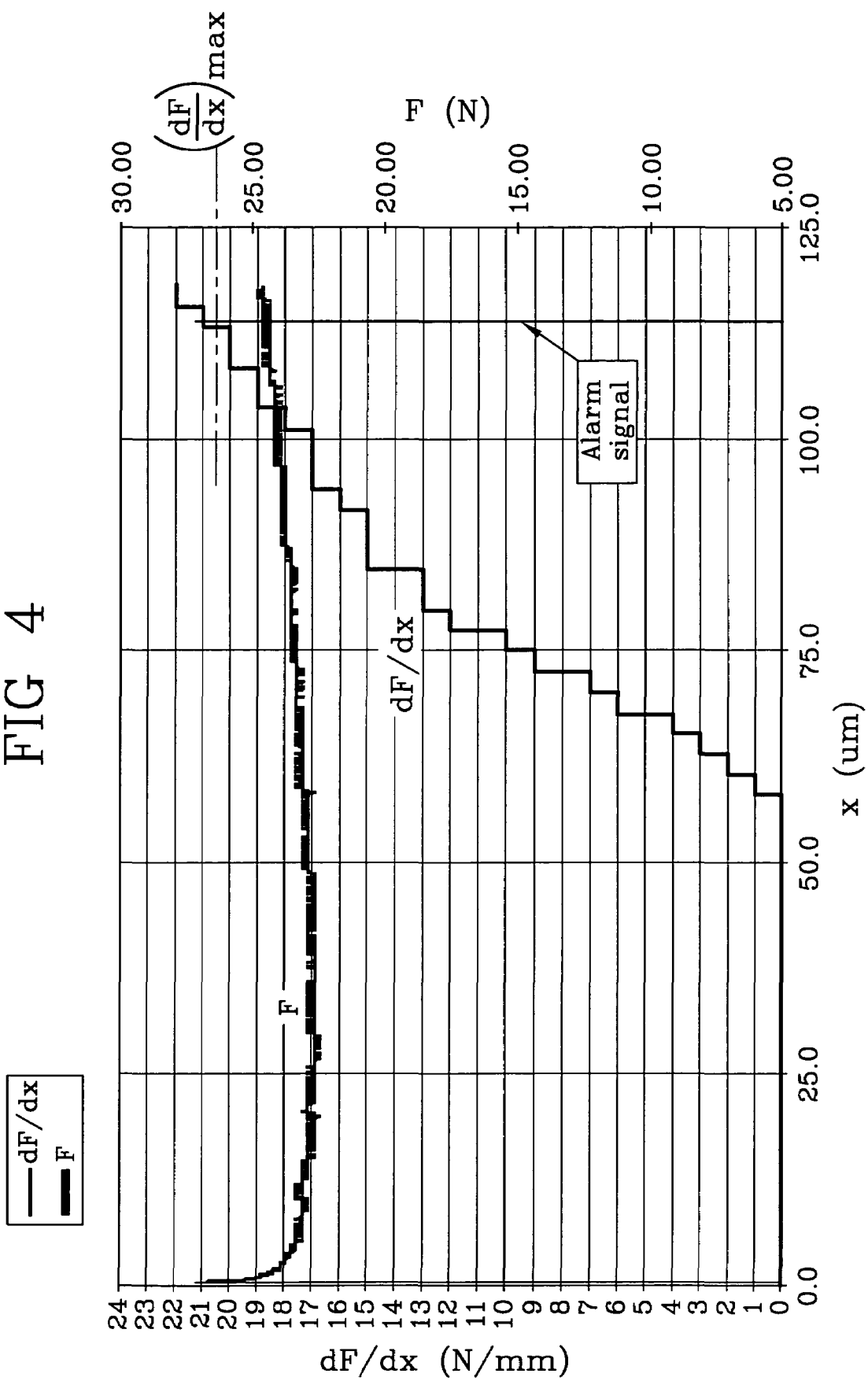
FIG. 4 is a diagram comprising a first curve representing the force applied on the pusher in accordance with the displacement of the pusher, and a second curve representing the derivative of the force with respect to the displacement.

The diagram of FIG. 4 shows the progress of the derivative dF/dx of force F with respect to the displacement of the pusher. When $dF/dx>(dF/dx)_{max}$, where $(dF/dx)_{max}$ is a predefined threshold value, an anomalous situation is signalled.

The controller 15 carries out a triple control, signalling an anomaly if $F>F_{max}$, or if $F<F_{min}$, or if $dF/dx>(dF/dx)_{max}$.

Figure 3:
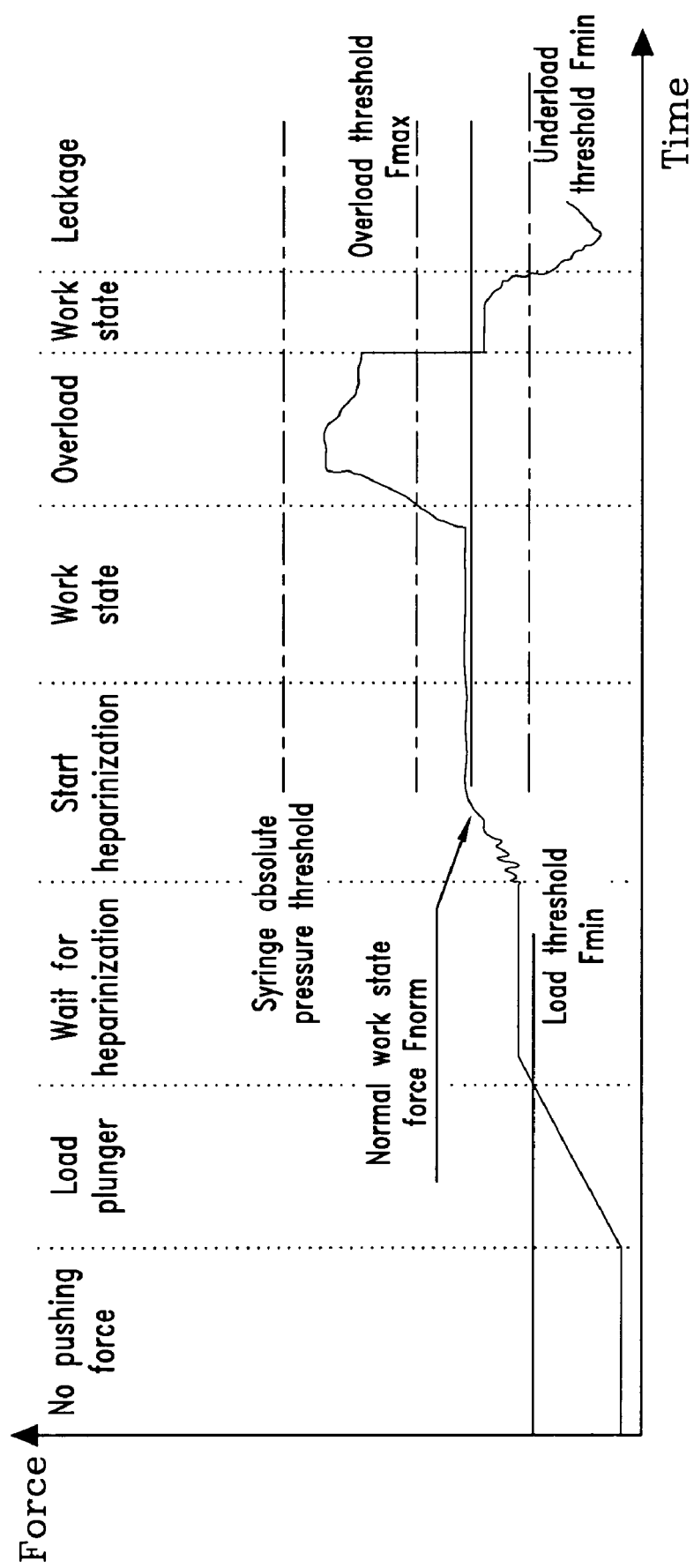
FIG. 3 is a diagram of the force applied on the pusher of the infusion device, over a period of time, during the various stages of the infusion process.

As illustrated in FIG. 3, the force measured by the sensor during the course of the various stages of the infusion of anticoagulant may vary.

The first stage, indicated by I, is the stage preceding the syringe loading (absence of push), in which the value of the force is inferior to a predefined threshold (load threshold $F_{min}$). The second stage, indicated by II, is the stage of syringe 6 loading, in which the pusher is advanced up until it contacts the plunger 9 and exceeds the threshold $F_{min}$; this is recognised by the controller 15 as the moment in which loading is complete.

At this point the infusion device 5 is ready for initiating the infusion of anticoagulant liquid into the extracorporeal circuit, though the actual start of infusion occurs only by direct order of the operator; this wait stage is indicated by III in FIG. 3 (wait for heparinization).

The controller 15, as mentioned, is able to acquire from the sensor 14 a value which is indicative of the resistant force which is effectively opposed to the pusher 10 advancement. The resistant force reaches stationary conditions after an initial transitory period, caused essentially by the friction variability on the plunger 9 at start of infusion. This transitory period can be seen in FIG. 3 from the irregular progression of the diagram in the initial part of stage IV (start heparinization stage).

The resistant force is a function of many parameters, among which the pressure of the fluid internally of the syringe, the cylinder section the plunger runs through, the type of syringe, the speed of advancement of the plunger and the plunger run.

During the course of the infusion, after the push force has reached a value which is considered to be stable (the force relating to normal operating conditions), a plurality of security measures is activated for detecting anomalous infusion situations. In particular, and among other things, at least three anomalous situations:

1. The force measured by the sensor 14 exceeds a prefixed value (over-pressure threshold); this situation can arise in the presence of an obstacle to the plunger advancement, or there may be an obstacle to liquid delivery into the extracorporeal circuit;
2. The force measured by the sensor 14 is lower than a prefixed threshold value (low load threshold); this situation may arise, for example, by effect of leakage in the infusion line, or detachment of the tube connecting the syringe with the extracorporeal circuit;
3. The derivative of the force measured by the sensor 14 as a function of the displacement measured by the encoder of the motor 13 is above a prefixed threshold; this situation may arise due to an occlusion in the tube which connects the syringe with the extracorporeal circuit, or other obstacles to infusion of the anticoagulant liquid in the extracorporeal circuit; it has been seen that the anomalous situation, in comparison with the causes outlined in point 1) above, is more rapidly reached than the anomalous situation of point 1).

In cases where one or more than one of these faults occur, the controller 15 is programmed to signal the risk of danger present to the control system on the dialysis machine.

The reference values for anomalous situations as in points 1 and 2 above (over-pressure and under-pressure thresholds) can be predetermined, or can be determined by the controller during the initial stage of heparinization; in particular, the controller can monitor the push force and calculate a value (indicated in FIG. 3 as a force at normal operating conditions=$F_{norm}$) in which the force is considered to be stabilised, for example by evaluating the derivative of the push force in relation to time and verifying when the derivative assumes a null value or a lower value than a small preselected reference value.

The overload threshold $F_{max}$ and/or the under-load threshold $F_{min}$ can be determined on the basis of the force $F_{norm}$ under normal operating conditions calculated, for example, as $F_{max}=F_{norm}+\Delta F_{sup}$, and $F_{min}=F_{norm}-\Delta F_{inf}$, where $\Delta F_{sup}$ and $\Delta F_{inf}$ are security values defining a band of admissibility of the push force around force $F_{norm}$ in the stabilisation situation.

Figure 5:
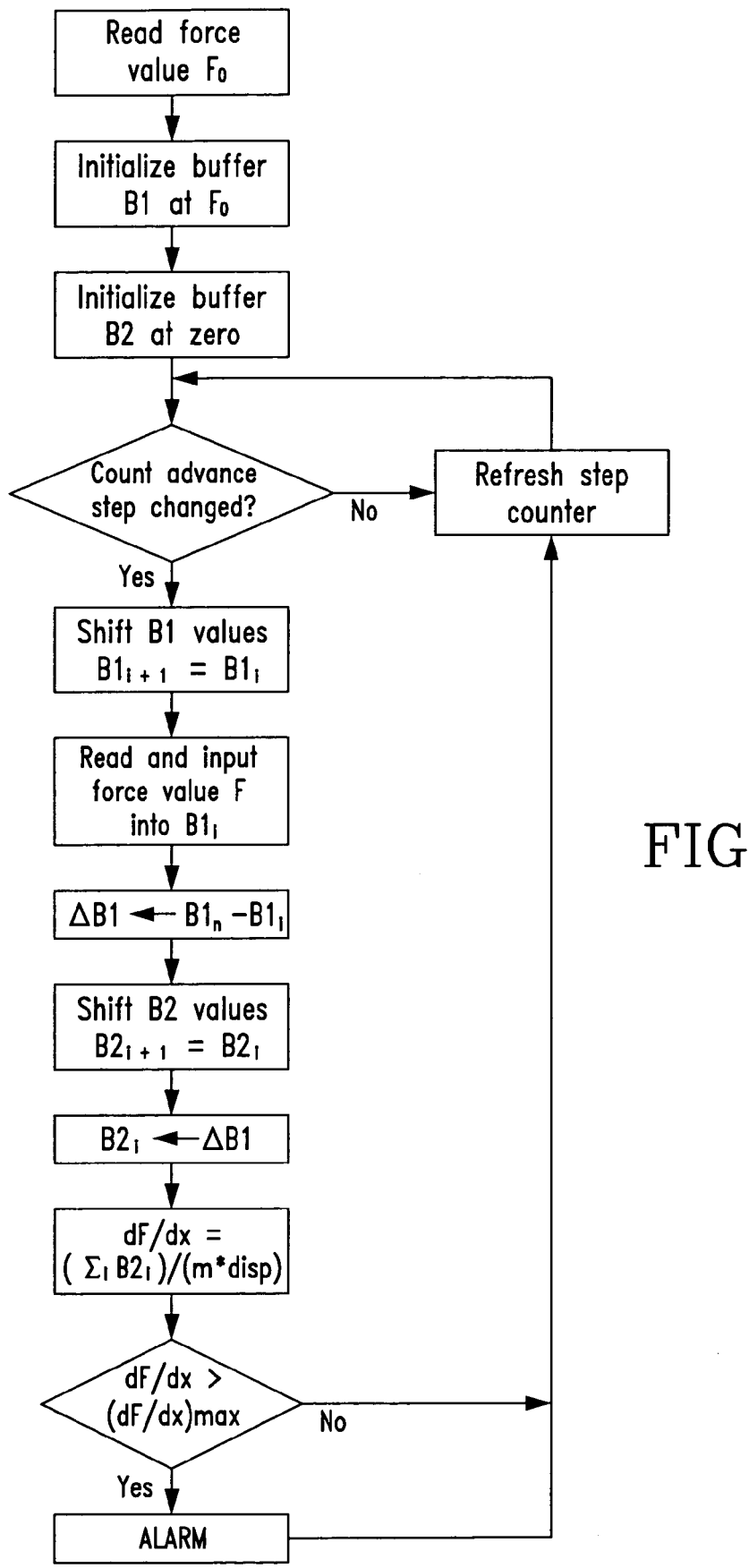
FIG. 5 is a block diagram describing the overpressure control algorithm of the infusion device.

The control algorithm used by the controller 15 for detecting the anomalous situation mentioned in point 3) above is described in the block diagram of FIG. 5. The control algorithm comprises the instructions for enabling the controller 15 to carry out the above-mentioned infusion control procedure.

The algorithm is constructed on the basis of one of the possible numerical calculation criteria for determining the derivative of a measured parameter; obviously it is possible to use other calculation criteria for the derivative, all known in the field of numerical calculation.

Figure 6:
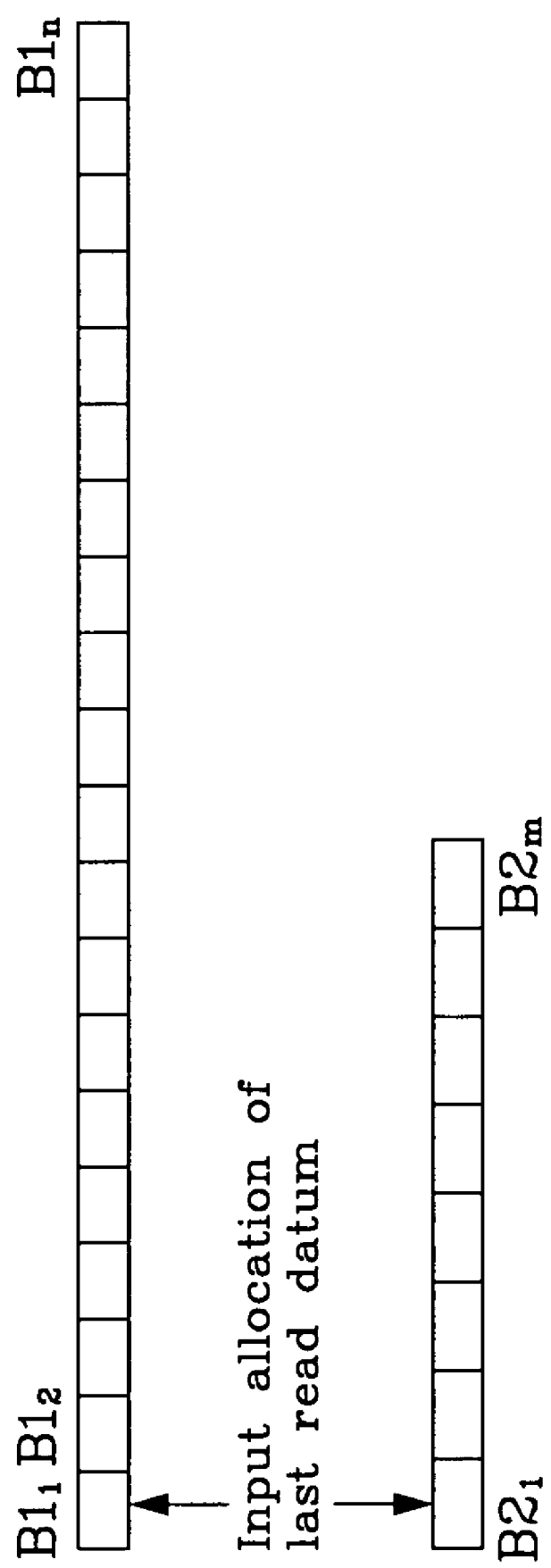
FIG. 6 is a diagram of the buffer memory used by the control algorithm of FIG. 5.

In the illustrated embodiment, the algorithm includes an initialisation stage of two circular buffers (see FIG. 6), a first buffer B1 of size n, i.e. composed of n memory allocations ($B1_1$, $B1_2$, $B1_3$, ..., $B1_i$, ..., $B1_n$), each of which is for memorising a measured force value, and a second buffer B2 of size m, composed of m memory allocations ($B2_1$, $B2_2$, $B2_3$, ..., $B2_i$, ..., $B2_m$). After the initialisation stage a check on the advancement by one step of the step motor is run; if the step has occurred, the algorithm posits $B1_{i+1}=B1_i$ (being i=n−1, n−2, ..., 2, 1), and therefore $B1_1=F$, where F is a value indicating the push force on the plunger, provided by the sensor 14. Each buffer B1 value is displaced upwards in the allocation (the content of $B1_i$ is shifted to $B1_{i+1}$).

The algorithm then calculates $\Delta B1=B1_n-B1_1$, posits $B2_{i+1}=B2_i$ (being i=m−1, m−2, ..., 2, 1, i.e., as with buffer B1, the content of $B2_i$ is shifted to $B2_{i+1}$), posits $B2_0=\Delta B1$, and calculates $$\frac{dF}{dx} = \frac{\sum_{i=1}^{m} B2_i}{m \cdot \Delta x}$$

where $\Delta x$ is the advancement run of the pusher at each motor step.

If $dF/dx>(dF/dx)_{max}$, the alarm is set off, otherwise the algorithm continues the operative cycle from the verification stage of the advancement by one step of the step motor.

The algorithm performing the control of the force is contained in a software program which can be memorised on a magnetic and/or optical support, or memorised in a computer memory, or on an electric or electromagnetic support, or in a read-only memory.

In cases of even partial occlusion of the infusion line, the control system based on monitoring the derivative of the infusion force on the plunger 9 on the basis of the displacement of the plunger 9 enables a timely signalling of the anomalous situation, which could cause a loss of infusion, to be given.

The invention claimed is:

1. A device for infusion of a liquid, comprising:
   an actuator for exerting an infusion force on the liquid to be infused;
   a first sensor for measuring at least a first parameter indicative of the infusion force;
   a second sensor for measuring a second parameter which is variable in accordance with the first parameter;
   a controller programmed to perform the following operations:
   determining at least two values of the first parameter, said first parameter being indicative of said infusion force, and determining at least one variation between said values of the first parameter,
   determining at least two values of the second parameter, said second parameter being indicative of a position of a mobile part of the actuator, and determining at least one variation between said values of the second parameter, said at least one variation of the second parameter is a displacement of the mobile part of the actuator,
   verifying whether said values of the first and second parameters are in a predetermined relation with a reference value, wherein the operation of verifying comprises verifying whether a ratio between the variation of the first parameter and said displacement exceeds a threshold value, and
   emitting a signal in consequence of the verification.

2. The device of claim 1, wherein the operation of emitting a signal comprises emitting an alarm signal if the ratio exceeds the threshold value.

3. The device of claim 1, wherein the controller is further programmed to verify whether a measured value of said first parameter is in a predetermined relation with a reference value.

4. The device of claim 1, wherein the first sensor comprises a force transducer.

5. The device of claim 1, wherein the actuator is a linear actuator.

6. The device of claim 1, wherein the actuator comprises a syringe pump.

7. A machine for extracorporeal blood treatment, comprising an infusion device according to claim 1.

8. The machine of claim 7, wherein the infusion device is configured to infuse an anticoagulant into an extracorporeal blood circuit.

9. The machine of claim 8, wherein the machine is configured to perform at least one of hemodialysis, pure ultrafiltration, hemofiltration, hemodiafiltration, plasmapheresis, hemoperfusion, and therapeutic plasma exchange.

* * * * *